United States Patent [19]

Kimura

[11] Patent Number: 4,490,359

[45] Date of Patent: Dec. 25, 1984

[54] QUALITY IMPROVER FOR ANIMAL FUR

[75] Inventor: Makoto Kimura, Tokyo, Japan

[73] Assignee: Eisai Co., Ltd., Tokyo, Japan

[21] Appl. No.: 451,321

[22] Filed: Dec. 20, 1982

Related U.S. Application Data

[63] Continuation of Ser. No. 274,361, Jun. 16, 1981, abandoned.

[30] Foreign Application Priority Data

Jun. 17, 1980 [JP] Japan .................................. 55-80906

[51] Int. Cl.³ .............................................. A61K 31/07
[52] U.S. Cl. ......................................... 424/93; 424/92
[58] Field of Search .................................... 424/92, 93

[56] References Cited

PUBLICATIONS

Cristofalo et al., Rivista d. Conigicoltura, 17, (2): 43–47, Feb. 1980.
Corino et al., Arch. Vet. Ital., 31, (6): 168–171, Dec. 1980.
Hayashi et al., Chem. Abstr., 87, #199767c, (1976).
Lab. Anphar., Chem. Abstr., 74, #139558j, (1969).
Hoogenraad, Chem. Abstr., 72, #108554j, (1970).
Burghardi, Chem. Abstr., 92, #213856, (1980).
Chah, Chem. Abstr., 85, #61785m, (1976).
Chah, Chem. Abstr., 83, #77390x, (1975).

*Primary Examiner*—Shep K. Rose
*Attorney, Agent, or Firm*—Wenderoth, Lind & Ponack

[57] ABSTRACT

A quality improver for animal fur which contains *Bacillus subtilis* var. *natto* as an active ingredient is administered to sheep, rabbits, minks etc. by adding it to animal feeds. The fur obtained has thinner and longer staples with an increased crimp number and is very fleecy.

5 Claims, No Drawings

QUALITY IMPROVER FOR ANIMAL FUR

This application is a continuation of Ser. No. 274,361, filed June 16, 1981, now abandoned.

BACKGROUND OF THE INVENTION

1. Field of the Invention

This invention relates to a quality improver for animal fur. More particularly, it relates to a quality improver for animal fur which contains *Bacillus subtilis* var. *natto* as an active ingredient.

2. Description of the Prior Art

Fur obtained from sheep, rabbits, cows etc. is utilized in large amounts as textile materials, felt materials etc. and what is important for animal raisers is enhancement of quantity and quality of fur. To produce as much fur of as high quality as possible is an important subject, and various studies have heretofore been done in order to achieve this object from the aspect of improvement of breed.

I have been intensively studying to discover a method to increase production of animal fur and improve its quality without relying on the above-mentioned improvement of breed. In other words, I have been studying for many years for the purpose of producing the greatest possible amount of fur of the highest possible quality per animal, such as sheep, rabbit etc. As a result, it has now been discovered that administration of *Bacillus subtilis* var. *natto,* added to animal feeds, to animals unexpectedly can produce large amounts of fur of high quality.

SUMMARY OF THE INVENTION

Accordingly, one object of this invention is to provide a quality improver for animal fur.

Another object of this invention is to provide a method to produce large amounts of animal fur of high quality.

DESCRIPTION OF THE PREFERRED EMBODIMENT

*Bacillus subtilis* var. *natto* used in this invention belongs to the species *Bacillus subtilis,* which is one of the most stable bacterial species in nature.

Examples of commerical products thereof are, for example, Growgen (commodity name) etc. This product is formulated into a preparation by adding pharmacopeia potato starch and contains $10^8$ or more spores of *Bacillus subtilis* var. *natto* strain BN per gram of the formulation. In this invention, any product which contains *Bacillus subtilis* var. *natto* in some form may be used, and any *Bacillus subtilis* var. *natto* used in production of fermented soybeans (*natto*) may be employed.

While the amount of *Bacillus subtilis* var. *natto* to be used for practicing this invention can vary depending on the kind of the animal, the other components of the feed etc. and thus cannot be stated unconditionally, *Bacillus subtilis* var. *natto* is generally administered in an amount of about $10^7$–$10^{10}$ spores per day added to animal feeds.

The animal for which this invention is contemplated may be any animal having fur, and specific examples thereof include those providing textile materials, felt materials, writing brush material, brush materials etc. such as sheep, rabbits, camels, cows, goats, pigs, horses and other livestock, those providing fur materials such as minks, weasels, foxes, raccoon, dogs and other fur animals, and pet animals such as dogs, cats, etc. Among the above, those of the greatest value from an economical view point are sheep, rabbits, goats and minks. In the case of sheep, representative examples include wool breed such as Rambouillet merino, Australian merino, American merino, Derain merino, Saxony merino, Schiredia merino, Hungarian merino, Hanover merino and other Merinos, wool and mutton breed such as Corriedale, Borarse, Roameldale, Corombia, Montadale, Panama, Perendale, Ideal, Karsdale, Waletenberg and wool breed such as Chinese sheep, Mongolian sheep, Romanoff, Karakul etc. Representative examples of rabbits are such species as Angora, Japanese white, New Zealand white etc. Representative examples of goats are wool breed such as Angora, Cashmere, etc. Representative examples of minks are Pastel, Sapphire, Dark species etc.

In the case of wool, that having longer and thinner staples and a greater crimp number is generally regarded as superior wool. The "crimp" is a phenomenon in which each wool staple exhibits waviness, twisted right and left along its longitudinal axis. The distance between the crest of one wave and the crest of the next wave is counted one, and the numerical value of such distances in a unit length is referred to as the crimp number. A greater crimp number improves the handfeel and touch of wool and enhances the heat retaining properties by forming a space between the staples, and therefore the crimp number is an important index to determine the quality of wool as a textile material.

By administering *Bacillus subtilis* var. *natto* to animals according to this invention, the fur yield and the fur quality thereof are enhanced and thus performance of fur production is greatly improved.

In other words, by practicing this invention, as demonstrated in the example given hereinbelow, it has now been made possible to produce fur having longer staples and a greater crimp number as well, and furthermore, it lends a very fleecy coat apparent to the naked eye, thus presenting outstanding beauty. Therefore, fur obtained from sheep, rabbits, camels etc. according to this invention is ideal as textile materials, and further, fur obtained from sheep, goats, minks, foxes, weasels, raccoon, dogs etc. is most suitable as fur materials. In addition, as described above, since this invention imparts a fine coat apparent to the naked eye and very attractive in appearance, this invention is also very desirable for use for pet animals such as dogs, cats etc.

*Bacillus subtilis* var. *natto* used in this invention is extremely economical, has no side effects and further *Bacillus subtilis* var. *natto* itself has a digestive effect, and therefore it is very desirable as an animal feed additive.

The effect of this invention is more particularly described in the following example.

EXAMPLE

Results of the Test on Sheep

1. Animals Tested

Ten 2-month-old male sheep naturally crossbred of Corriedale species and Safolk species, each weighing approximately 25 kg, were used.

2. Raising

The animals were individually raised in each sheep cage of 1.7 m × 1.7 m, 2.89 m$^2$.

3. Animal Feed Supplied

A concentrated feed for cows (a feed for fatting cows in the later stage; commodity name: New King Beef) and hay were used. The ratio of the components of the hay and feed are set forth in Table 1 below.

TABLE 1

| Animal Feed | Component | | | | | | |
|---|---|---|---|---|---|---|---|
| | Water Content | Crude Protein | Crude Fat | Crude Fiber | NFE | Crude Ash | Total |
| Hay | 15.06 | 7.21 | 1.70 | 33.97 | 37.71 | 4.35 | 100.00 |
| Concentrated Animal Feed | 15.50 | 11.54 | 1.51 | 1.05 | 65.90 | 4.50 | 100.00 |

4. Method of Administration

A *Bacillus subtilis* var. *natto* preparation (commodity name: Growgen 8) added to the above-described concentrated feed in an amount of 10 g per day per animal, i.e. $10^9$ or more spores of *Bacillus subtilis* var. *natto* strain BN, was administered for 4 months.

5. Test Result

Four months later, the staple length, staple thickness and crimp number of each sheep were measured. The results are given in Tables 2-4 below respectively.

TABLE 2

Staple Length of Sheep on the Neck Side (cm)

| Group | Sheep No. | | | | | Mean Value ± Standard Deviation |
|---|---|---|---|---|---|---|
| | 1 | 2 | 3 | 4 | 5 | |
| Control Group | 6.3 | 7.5 | 6.8 | 7.8 | 8.0 | 7.28 ± 0.71 |
| Test Group | 10.1 | 10.2 | 9.6 | 8.9 | 10.3 | 9.82 ± 0.58*** |

***P < 0.001

TABLE 3

Staple Thickness (average Diameter of 20 staples, μ)

| Group | Sheep No. | | | | | Mean Value ± Standard Deviation |
|---|---|---|---|---|---|---|
| | 1 | 2 | 3 | 4 | 5 | |
| Control Group | 35.4 | 32.5 | 34.5 | 32.0 | 31.8 | 33.24 ± 1.61 |
| Test Group | 28.0 | 27.2 | 30.2 | 31.5 | 26.9 | 28.76 ± 2.00** |

TABLE 3-continued

Staple Thickness (average Diameter of 20 staples, μ)

| Group | Sheep No. | | | | | Mean Value ± Standard Deviation |
|---|---|---|---|---|---|---|
| | 1 | 2 | 3 | 4 | 5 | |

**P < 0.01

TABLE 4

Crimp Numbers per Inch

| Group | Sheep No. | | | | | Mean Value ± Standard Deviation |
|---|---|---|---|---|---|---|
| | 1 | 2 | 3 | 4 | 5 | |
| Control Group | 9 | 9 | 9 | 9 | 10 | 9.2 ± 0.45 |
| Test Group | 10 | 10 | 10 | 10 | 11 | 10.2 ± 0.45** |

**P < 0.01

As evident from Table 2, the staple length of the test group was about 2.5 cm longer as compared with that of the control group.

As evident from Table 3, the thickness of the test group was about 4.5 μ thinner as compared with that of the control group.

As evident from Table 4, the crimp number per inch of the test group was about one larger than that of the control group.

In addition, macrographic observation also revealed that the sheep of the test group had finer and more fleecy coats and better physiques as compared with those of the control group.

As demonstrated by the above experimental example, since this invention enables production of fur having thinner and longer staples with an increased crimp number, and in addition the fur obtained is very fleecy as apparent to the naked eye and hence presents outstanding beauty, such fur is ideal for wool etc. Therefore, this invention is of great value.

What is claimed is:

1. A method of enhancing production of fur in rabbits or minks, or wool in sheep, which comprises administering orally to the animal an amount of *Bacillus subtilis* var. *natto* strain BN sufficient to enhance production of fur or wool on the animal.

2. A method according to claim 1, wherein the animal is a rabbit.

3. A method according to claim 1, wherein the animal is a mink.

4. A method according to claim 1, wherein $10^7$ to $10^{10}$ spores of *Bacillus subtilis* var. *natto* strain BN is administered to the animal per day.

5. A method according to claim 1, wherein the animal is a sheep.

* * * * *